United States Patent [19]
Andreiko

[11] Patent Number: 5,376,002
[45] Date of Patent: * Dec. 27, 1994

[54] METHOD OF FORMING AND DENTAL BRACKET OF NICKEL-CHROMIUM-BERYLLIUM BASED ALLOYS

[75] Inventor: Craig A. Andreiko, Alta Loma, Calif.

[73] Assignee: Ormco Corporation, Glendora, Calif.

[ * ] Notice: The portion of the term of this patent subsequent to Oct. 19, 2010 has been disclaimed.

[21] Appl. No.: 110,546

[22] Filed: Aug. 23, 1993

Related U.S. Application Data

[63] Continuation of Ser. No. 844,794, Mar. 2, 1992, Pat. No. 5,254,003.

[51] Int. Cl.⁵ ............................................. A61C 3/00
[52] U.S. Cl. ................................... 433/9; 29/160.6
[58] Field of Search ................ 433/8, 9, 24; 29/160.6

[56] References Cited

U.S. PATENT DOCUMENTS

| | | | |
|---|---|---|---|
| 4,592,890 | 6/1986 | Burnett et al. | 433/207 |
| 4,673,354 | 6/1987 | Culler | 433/217.1 |
| 4,978,391 | 12/1990 | Jones | 433/8 |
| 5,011,410 | 4/1991 | Culler et al. | 433/218 |

OTHER PUBLICATIONS

S. A. Aquilino et al., "Tensile Fatique Limits of Prosthodontic Adhesives", J Dent Res, Mar. 1991, pp. 208–210.
The Critical Role of Rexillium III in Acid–Etched Bridgework, Jeneric Gold Co.
Rexillium III paper on physical properties.

Primary Examiner—John J. Wilson
Attorney, Agent, or Firm—Wood, Herron & Evans

[57] ABSTRACT

A dental bracket is made from an alloy of nickel, beryllium and chromium. The alloy may be that designated by the trademark REXILLIUM III. A groove is disposed in one surface of the bracket to receive an arch wire. An opposite surface of the bracket is roughened to receive an adhesive which has properties of adhering to the bracket and to a patient's tooth. The bracket is formed by heating the alloy to the molten state, pouring the molten alloy into a mold with a cavity in the shape of the bracket and allowing the bracket to cool in air to room temperature. As the bracket cools, the beryllium oxide formed during the heating of the alloy is formed into dendrites. The surface receiving the adhesive is washed with an acid to remove the material in the space between the dendrites and thereby roughen the surface for the reception of the adhesive. The dental bracket is advantageous in that it is made from a single integral piece of material and in that it has properties of preventing tarnishing when scratched. This results from the oxidation of the beryllium oxide during the formation of the bracket and the migration of the beryllium oxide to the surface area where the scratch is located.

3 Claims, 1 Drawing Sheet

METHOD OF FORMING AND DENTAL BRACKET OF NICKEL-CHROMIUM-BERYLLIUM BASED ALLOYS

This application is a continuation of application Ser. No. 07/844,794, filed Mar. 2, 1992, now U.S. Pat. No. 5,254,003.

This invention relates to a dental bracket and more particularly relates to a dental bracket made from a single integral piece of material with properties of adhering positively to a tooth and of preventing tarnishing when the dental bracket is scratched.

Dental brackets are used to reposition the teeth of a patient so that the cusps in the lower bicuspids will fit into the ridges in the upper bicuspids. Hopefully this repositioning of the patient's teeth will allow the teeth to be retained in good condition for many years in the patient's mouth and will allow the patient's gums to remain in good condition.

The dental brackets now in use are generally formed from more than one (1) member. For example, each bracket generally includes a support member and a pad. The support member is made from a suitable material such as stainless steel and is provided with a groove in one surface to receive an arch wire. The arch wire is disposed in the groove to apply a force to the tooth to move the tooth to the desired position in the patient's mouth. A pad made from a suitable metallic mesh such as a stainless steel mesh is attached to the opposite surface of the support member. An adhesive is disposed in the mesh pad to adhere the mesh pad to the support member and to the patient's tooth.

There are several disadvantages with the brackets now in use. One disadvantage is that the brackets are formed from more than one member. This increases the cost and inconvenience of forming each bracket. Furthermore, the mesh pad is included in the bracket for attachment to the support member and to the patient's tooth. Because of the mesh in the pad, approximately only thirty percent (30%) of the surface area of the bracket is available to receive the adhesive. This limits the locking force which can be applied between the bracket and the patient's tooth to attach the bracket to the tooth.

Bridges are used to position artificial teeth in a patient's mouth fixedly with respect to adjacent teeth in the patient's mouth. In an article entitled "Tensile Fatigue Limits of Prostohodontic Adhesives" prepared by S. A. Aquilino, A. M. Diaz-Arnold and T. J. Piotrowski and published in Vol. 70, No. 3, of the *Journal of Dental Research* in March, 1991, at pages 208–210, a material designated by the trademark REXILLIUM III is described for use in such bridges.

This invention provides a bracket formed from a single unitary member. The member is formed at the surface facing the tooth so that substantially all of the area of the bracket is available to be bonded as by adhesive to the tooth. This enhances the bonding force between the bracket and the tooth. The bracket is also advantageous in that it is formed from a material which prevents the bracket from tarnishing in a patient's tooth if the surface of the bracket should inadvertently be scratched.

In one embodiment of the invention, a dental bracket is made from an alloy of nickel, beryllium and chromium. A groove is disposed in one surface of the bracket to receive an arch wire. An opposite surface of the bracket is roughened to receive an adhesive which has properties of adhering to the bracket and to a patient's tooth. The alloy may be that designated by the trademark REXILLIUM III, which is described in detail in the product specification sheet available from the manufacturer, Rx Jeneric Gold Co. of Wallingford, Conn., the content of which is hereby expressly incorporated herein by reference. As described in the specification sheet, REXILLIUM III is a non-precious nickel-chromium-beryllium alloy preferably containing about 1.8 weight percent beryllium. Additional properties of REXILLIUM III include:

| | |
|---|---|
| Brinell Hardness | 240 |
| Proportional Limit | 74,000 psi, 520 kg/mm$^2$ |
| Ultimate Tensile Strength | 155,000 psi, 1090 kg/mm$^2$ |
| Elongation | 9–12% |
| Melting Range | 2250–2350° F., 1232–1238° C. |
| Modulus of Elasticity | 28 × 10$^6$ psi, 198,000 kg/mm$^2$ |
| Specific Gravity | 7.75 gm/cc |

The bracket is formed by heating the alloy to the molten state, pouring the molten alloy into a mold with a cavity in the shape of the bracket and allowing the bracket to cool in air to room temperature. As the bracket cools, the beryllium oxide formed during the heating of the alloy is formed into dendrites. The surface receiving the adhesive is washed with an acid to remove the material in the space between the dendrites and thereby roughen the surface for the reception of the adhesive.

The dental bracket is advantageous in that it is made from a single integral piece of material and that it has properties of preventing tarnishing when scratched. This results from the oxidation of the beryllium oxide during the formation of the bracket and the migration of the beryllium oxide to the surface area where the scratch is located.

Figure 1:
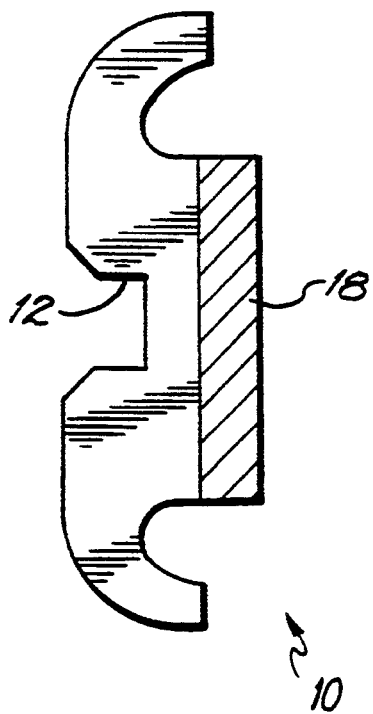
FIG. 1 is a sectional view of a dental bracket constituting one embodiment of the invention.
Figure 2:
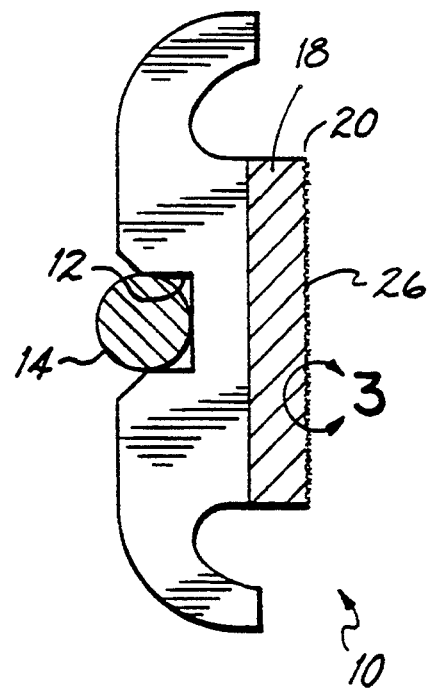
FIG. 2 is a sectional view similar to that shown in FIG. 1 but shows an arch wire in a groove in the bracket.

In one embodiment of the invention, a bracket generally indicated at 10 is made from a nickel-chromium-beryllium alloy. This alloy may be that designated as REXILLIUM III, available from the Rx Jeneric Gold Company of Wallingford, Conn., and described in detail hereinabove. As will be seen, the bracket 10 is a unitary member and is provided with a groove 12 for receiving an arch wire 14. The groove 12 is provided with an individual configuration, such as a width and a depth, dependent upon the force to be imposed on a patient's tooth 16 by the arch wire to reposition the tooth to an optimal position in a patient's mouth.

A surface 18 on the bracket 10 opposite the groove 12 is roughened or pitted as at 20 to receive an adhesive 22 which is bonded to such surface and to a patient's tooth 16. A suitable adhesive may be a 4 META adhesive system, which consists of 5% 4-methacryloxyethyl trimellitate anhydride and 95% polymethylmethacrylate initiated by tri-n-butyl borane. A filled BIS-GMA system with methacrylates and a phosphate ester added to the monomer may also be used. The use of such adhesives with the REXILLIUM III material is described in the articles specified above.

The bracket 10 may be formed by heating the alloy to a suitable temperature such as approximately 2400° F. to provide the alloy in a molten state. The molten alloy is then poured into a mold having a cavity with the shape of the bracket 10. The alloy is then allowed to cool in air to room temperature and the bracket may then be removed from the mold. By such a procedure, the beryllium in the alloy is oxidized to form beryllium oxide in the form of dendrites 26 near the surface of the bracket. The dendrites are strong and hard.

Figure 3:
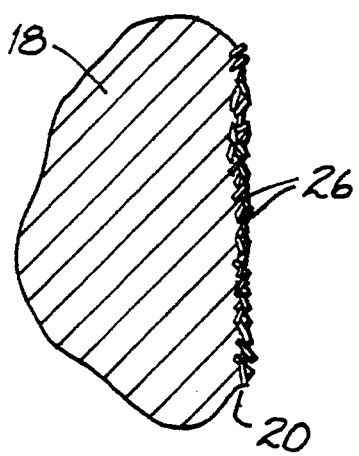
FIG. 3 is a schematic view of a surface of the bracket shown by encircled area 3 shown in FIG. 2, this surface being roughened or pitted to receive an adhesive for attaching this surface to a patient's tooth.
Figure 4:
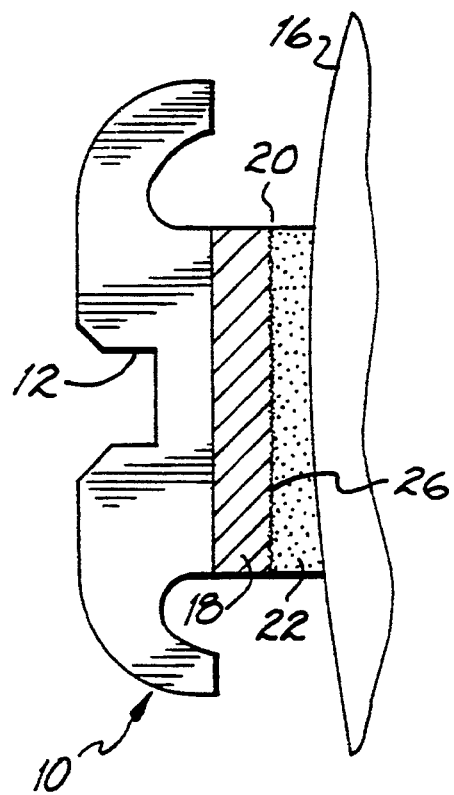
FIG. 4 is a schematic view of the bracket shown in FIGS. 1 and 2 after the attachment of the bracket to the patient's tooth.

The material at the surface 18 between the beryllium oxide dendrites may then be removed as by an acid wash. This removal is facilitated by the fact that the dendrites are under stress so that the acid is able to penetrate into the space between the dendrites and remove the material in this space. This causes the surface 18 to be roughened or pitted as illustrated at 20 in FIG. 3.

Before the acid wash is applied to the bracket 10, the surface 18 to be etched is abraded with particles of aluminum oxide of fifty microns (50μ) size at an air pressure of 80 psi. The acid wash may then be obtained by providing (a) a quart of concentrated hydrochloric acid and (b) a quart of hydrochloric acid in methanol. The bracket 10 is initially disposed in solution (b) and then solution (a) is poured into solution (b). The bracket is then retained in this mixture for approximately ten (10) minutes.

The bracket described above has certain important advantages. It provides a unitary integral structure which is hard and strong. The bracket 10 can be positively attached to the patient's tooth 16 because the adhesive 22 covers the entire area of the surface 18. This provides for a strong bond between the bracket and the tooth. In addition to being hard and strong and providing for the roughening of the surface 18, the beryllium oxide is advantageous because it migrates to the surface of the bracket and prevents the surface from tarnishing at any position where the surface of the bracket may be scratched.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. An article for application to a patient's tooth to support an arch wire, comprising:
   a metal dental bracket of nickel-chromium-beryllium based alloy having a groove for receiving an arch wire, said bracket having a surface for bonding to a tooth, said surface including a metallic oxide containing beryllium oxide.

2. A dental bracket for attachment to a patient's tooth, comprising:
   a metal bracket body of nickel-chromium-beryllium based alloy having a groove for receiving an arch wire, said bracket body having a bonding surface containing a metallic oxide, including beryllium oxide.

3. A method of making a dental bracket, comprising the steps of:
   molding molten a nickel-chromium-beryllium based alloy into the form of a dental bracket having a bonding base surface; and
   cooling the molded bracket such that a dendrite structure containing metallic oxide, including beryllium oxide, is formed on at least said bonding base surface.

* * * * *